United States Patent [19]

Knoth et al.

[11] Patent Number: 4,847,882
[45] Date of Patent: Jul. 11, 1989

[54] ARRANGEMENT FOR THE NON-DESTRUCTIVE MEASUREMENT OF METAL TRACES

[75] Inventors: Joachim Knoth, Hamburg; Harald Schneider, Geesthacht; Heinrich Schwenke, Echseburg, all of Fed. Rep. of Germany

[73] Assignee: GKSS Forschungszentrum Geesthacht GmbH, Geesthacht, Fed. Rep. of Germany

[21] Appl. No.: 19,815

[22] Filed: Feb. 27, 1987

[30] Foreign Application Priority Data

Mar. 1, 1986 [DE] Fed. Rep. of Germany ....... 3606748

[51] Int. Cl.$^4$ .......................................... G01N 23/223
[52] U.S. Cl. ........................................ 378/44; 378/45; 378/49
[58] Field of Search ................. 378/45, 44, 46, 48, 378/49

[56] References Cited

U.S. PATENT DOCUMENTS

| | | | |
|---|---|---|---|
| 4,169,228 | 9/1979 | Briska et al. | 378/45 |
| 4,358,854 | 11/1982 | Marten et al. | 378/45 |
| 4,426,717 | 1/1984 | Schwenke et al. | 378/45 |

FOREIGN PATENT DOCUMENTS 2911596 3/1986 Fed. Rep. of Germany .

Primary Examiner—Carolyn E. Fields
Assistant Examiner—David P. Porter
Attorney, Agent, or Firm—Spencer & Frank

[57] ABSTRACT

The present invention relates to an arrangement for the non-destructive measurement of metal traces in the surface of material samples in which the surface is irradiated with X-ray radiation and a detector, fastened above the material sample, spectrometrically examines the fluorescent radiation emanating from the material sample. Metal impurities are detected in the surface of, for example, silicon wafers down to about $10^{11}$ atoms/cm$^2$, on-line, with the wafers being free from contamination by the measuring process. It is possible to sweep the entire surface area of wafers having a diameter up to about 150 mm at the locations fixed by the respective standards. The X-ray radiation directed onto the surface of the material sample by means of an adjustable X-ray source, the divergence of the exciting X-ray radiation being limited by two aperture members, the aperture members being disposed in a quartz body serving as an optical bench. A positioning device is provided with which the material sample can be pressed against a surface of the quartz body.

5 Claims, 6 Drawing Sheets

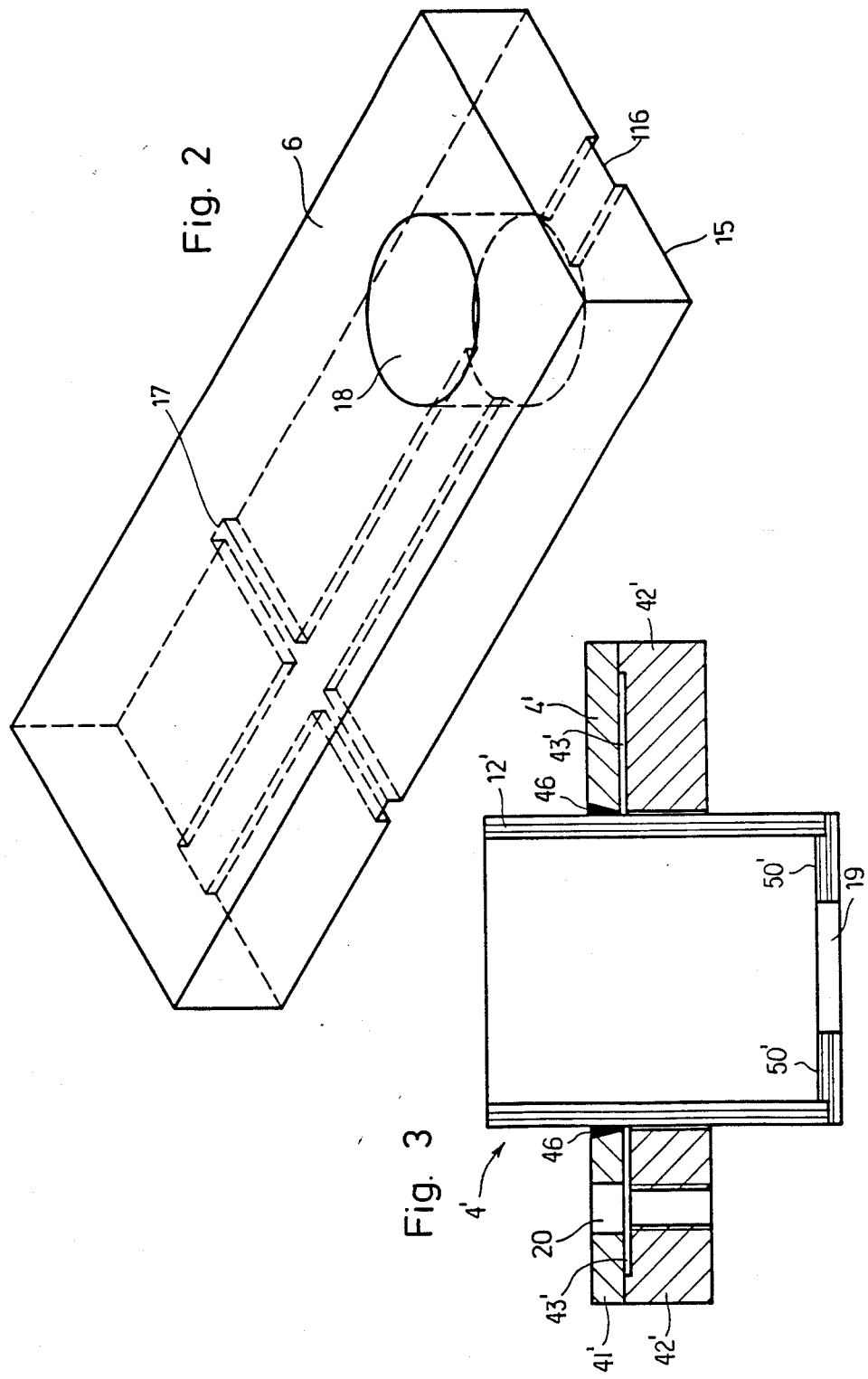

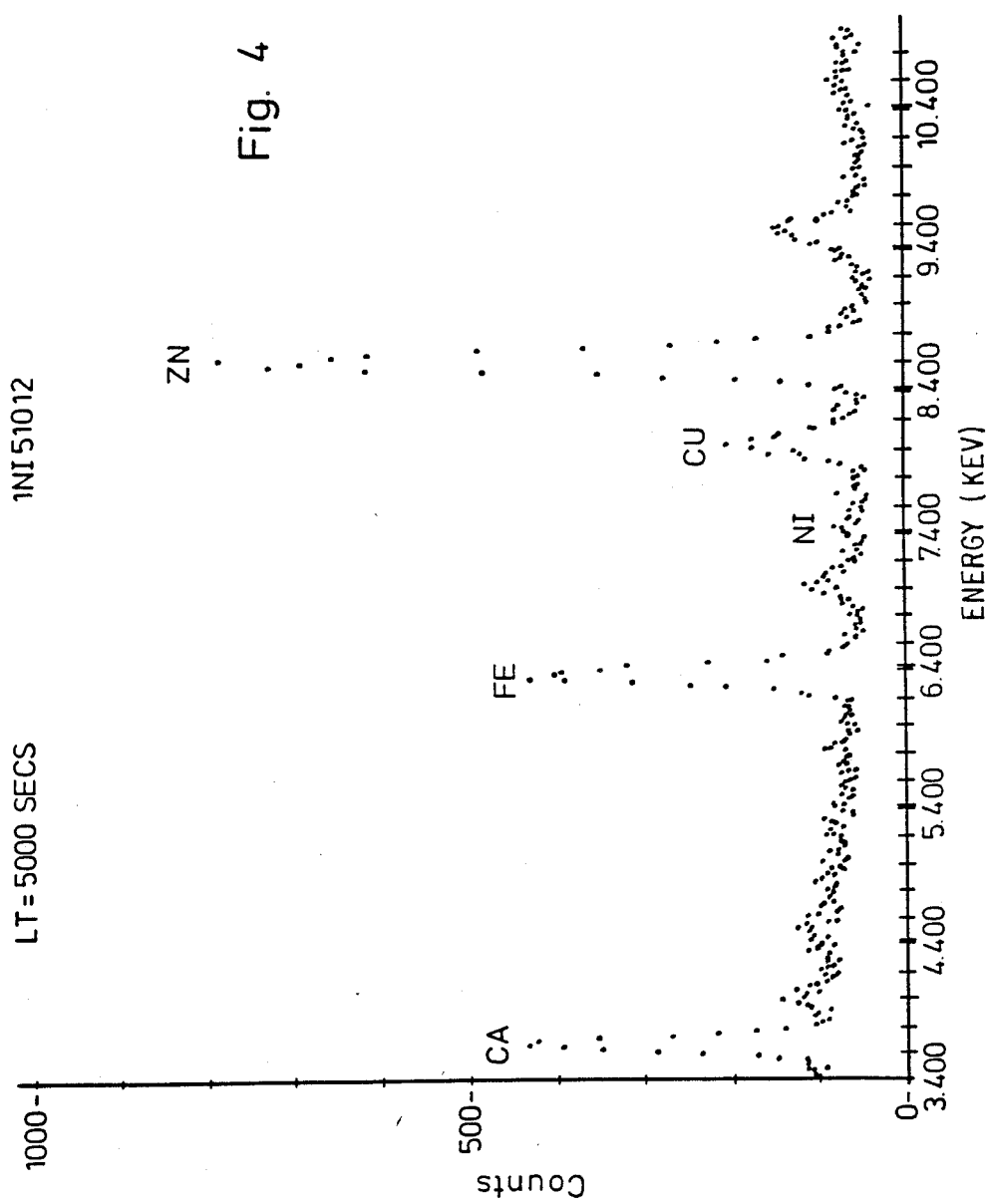

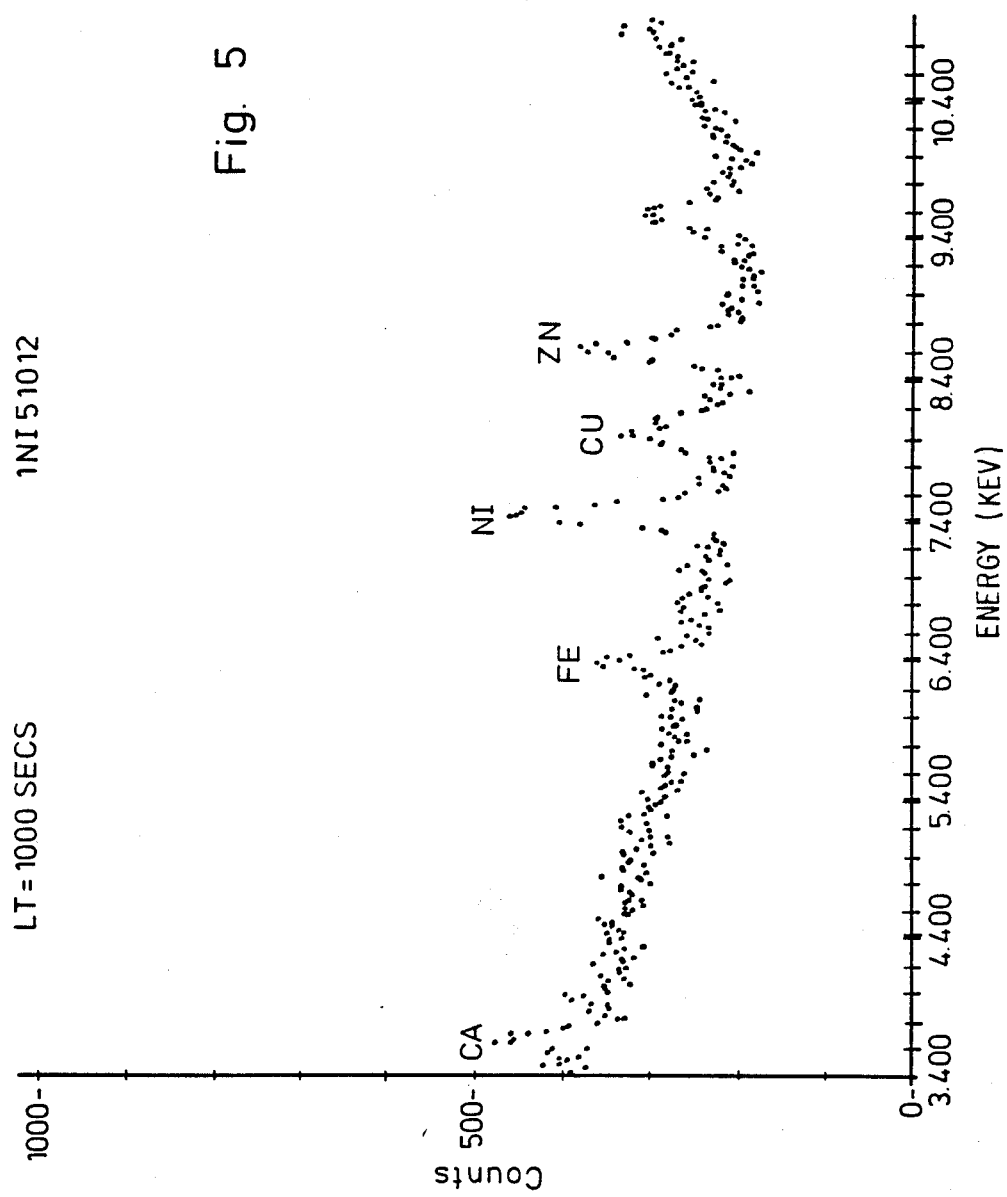

Fig. 6
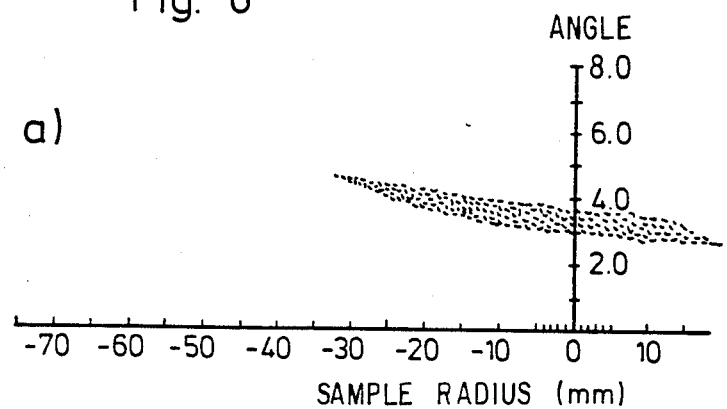
a)
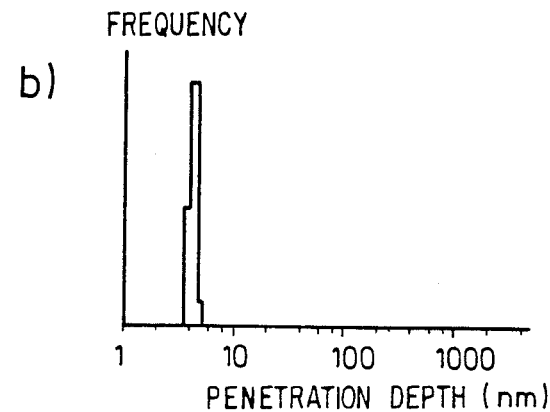
b)
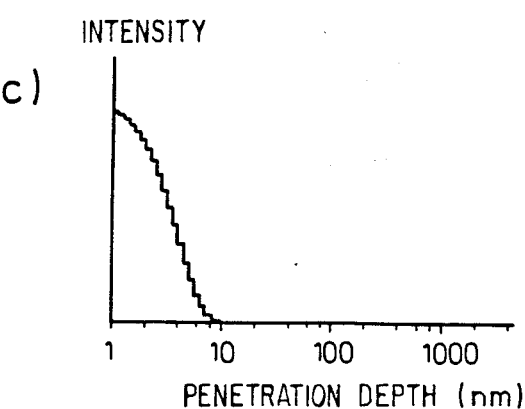
c)

Fig. 7
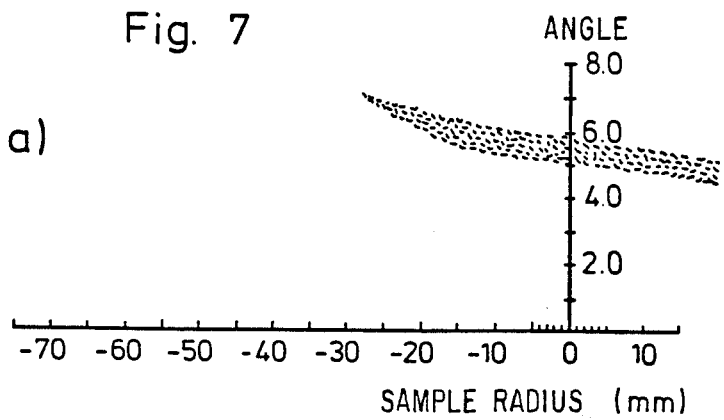
a)
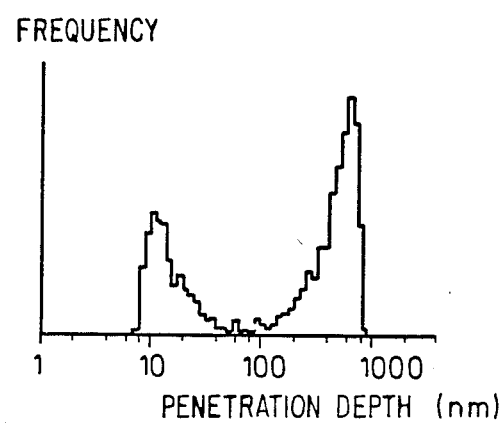
b)
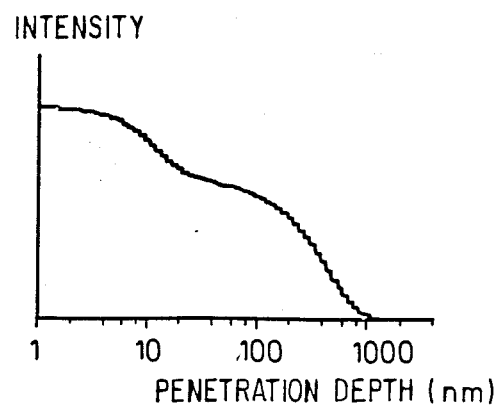
c)

ARRANGEMENT FOR THE NON-DESTRUCTIVE MEASUREMENT OF METAL TRACES

BACKGROUND OF THE INVENTION

FIELD OF THE INVENTION AND BRIEF DESCRIPTION OF THE PRIOR ART

The present invention relates to an arrangement for the non-destructive measurement of metal traces in the surface of material samples in which the sample surface is irradiated with X-ray radiation to provide flourescent radiation. A detector is positioned above the material sample to spectrometrically examine the flourescent radiation emanating from the material sample therein. Such X-ray radiation sweeps over the surface of the material sample from an adjustable X-ray source oriented toward the sample. The divergence of the exciting X-ray radiation is limited by means of two apertured members, these members being arranged at a quartz body serving as an optical bench. Such an arrangement is disclosed in DE-AS No. 2,911,596, which corresponds to U.S. Pat. No. 4,426,717, which is incorporated herein by reference.

Silicon wafers are the basis of highly integrated electronic components. Their purity must meet extreme requirements. These purity requirements are difficult to meet by production processes, particularly for the wafer surfaces, and therefore product monitoring is required. However, there is no measuring procedure in the prior art which permits on-line, non-destructive testing for impurities in such surfaces down to about $10^{11}$ atoms/cm$^2$.

Although it is possible, with the above-mentioned prior art arrangement, utilize the effects occurring upon the total reflection of X-ray radiation to examine surfaces with sufficient sensitivity, this arrangement is suitable only for surfaces having a maximum diameter of about 50 mm. Moreover, with the prior art structural solution, contamination of the test object from contact with the metal components of the instruments is possible.

SUMMARY OF THE INVENTION

It is an object of the present invention to detect and measure metal impurities in the surface of, for example, silicon wafers down to about $10^{11}$ atoms/cm$^2$, on-line with the wafers being free from contamination caused by the measuring process and with the possibility of scanning the entire surface area of wafers having a diameter up to about 150 mm at defined locations by the respective standards.

The present invention is a structural solution which permits utilization of the effect of the total reflection of X-rays at planar surfaces such that it is possible, for the first time, to examine the surfaces of the largest presently employed silicon wafers regarding their metal impurity content in a range of $10^{11}$ atoms/cm$^2$ without their destruction and contamination. This is realized, inter alia, by the use of a quartz block as the optical bench.

BRIEF DESCRIPTION OF THE DRAWINGS

FIG. 2 is a perspective view of quarterly body 6;

FIG. 3 is an enlarged view of the detector and an alternative embodiment of the associated structure;

FIGS. 4 and 5 are graphs showing the results of measurements to determine type and quantity of surface impurities; and FIGS. 6a to 6c and 7a to 7c show the results of calculations for two structures according to the present invention.

DESCRIPTION OF THE PREFERRED EMBODIMENT

The invention will be described in greater detail below with reference to an embodiment that is illustrated in FIGS. 1 to 7.

Figure 1:
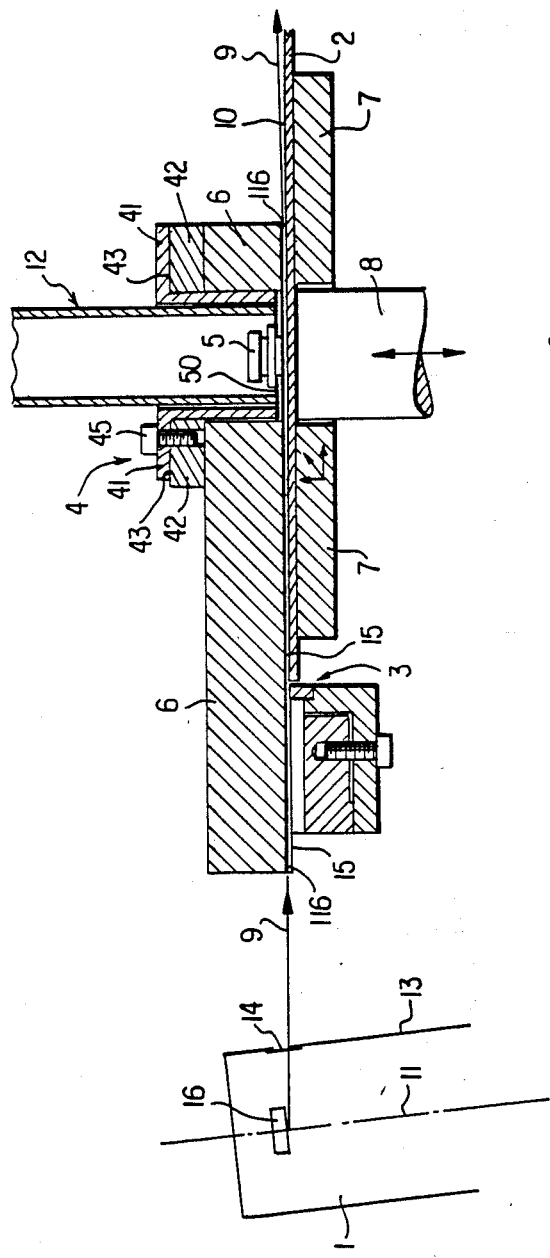
FIG. 1 is a partially schematic and partially sectional view of a system in accordance with the present invention.

FIG. 1 is a partially schematic and partially sectional view of an arrangement with which the surface of Si wafers can be tested and measured. Radiation 9 from an X-ray tube 1 is directed to sweep the surface 10 of an object 2 to be examined, in this case a silicon wafer, at an angle of a few arc minutes. The effective angle of incidence of radiation 9 with surface 10 is α' (this angle is not shown), and is set by changing the height 11 of X-ray tube 1, the divergence of the incident beam 9 being limited by two apertured members 3 and 4. If the set angle of incidence lies below the limit angle for total reflection, the exciting radiation 9 penetrates only slightly into wafer (about 10 nm) so that only the atoms of the uppermost surface layer thereof are excited to emit flourescent radiation. This flourescent radiation is collected by a detector 5 and identified and quantified by means of a known technique in X-ray flourescence analysis which forms no part of this invention. Detector 5 is disposed within a shield 12 which is secured to the apertured member 4 and is oriented perpendicularly to the surface 10 of wafer 2.

The significant components of the invention include an adjustable tube mount 13 of the X-ray tube 1 equipped with an exit aperture 14, a specially prepared quartz block 6 the structure of which is shown in FIG. 2. to which are attached the two apertured members 3 and 4 which are of special design (the structures of which are described hereunder and are shown in FIGS. 1 and 3) and are adjustable within the μm range, as well as a positioning device equipped with a pressing piston 8 for pressing against the wafer 2 and a device 7 for pressing the wafer surface 10 against a planar polished surface 15 at the underside of quartz block 6.

As seen in FIG. 1, the apertured member 4 includes a pair of cooperating elements 41 and 42 which are adjustable relative to one another by means of a screw 45 which engages in a threaded bore (unnumbered) in the portion 42. The screw 45 causes adjustment of a relatively fine gap 43 (which is similar to a gap 43' shown in detail in FIG. 3, as described hereunder). Also as seen in FIG. 1, the shield 12 is supported by a member 50, the member 50 having the aforementioned aperture therein which receives the detector 5 (as shown in detail in FIG. 3 showing a closely related embodiment, discussed hereunder). The member 50 is connected to the portion 41. Since FIG. 1 is a sectional view which, as seen from FIG. 2, is taken along a center of a slot 116 and a bore 18 which receives the apertured member 4, a side wall of the slot 116 is visible in elevation in FIG. 1.

Apertured member 3 includes portions 31 and 32 having a gap 34 which is adjustable by a screw 35 in a manner similar to that described hereinabove with respect to the gap 43 and screw 45. A wall 36 is disposed between the surface 15 and the portion 32 of the apertured member 3. The portion 31 carries a shielding member 33 which, as described hereunder, blocks the radiation 9 from entering the left-hand side face of the wafer 2. Thus, the radiation 9 can strike only the surface of the wafer 2, also as discussed further hereunder.

Figure 1A:
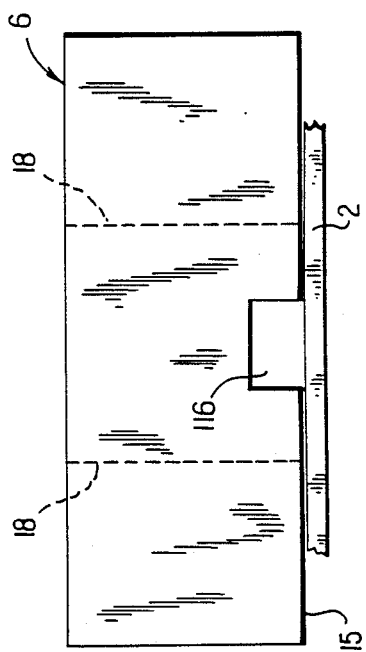
FIG. 1A is a right-hand elevational view, shown highly schematically and not to scale, of a quartz block and a material sample of the system of FIG. 1.

FIG. 1A is a right-hand elevational view of the quartz block 6 and the wafer 2 as they would be seen from the right of FIG. 1. The drawing is not shown to scale, but rather shows the channel 116 in an exaggerated size for clarity. The contact of the upper face of the wafer 2 with the lower face 15 of the quartz body 6 is clearly shown in this drawing. The bore 18 in the quartz body 6 is seen in dotted outline in this figure, which omits other structures seen in FIG. 1 for clarity.

Quartz block 6 (FIG. 2) serves as an optical bench whose planar surface 15, which is resistant to bending, is utilized as a highly accurate reference surface. The wafer surface 10 is aligned by pressing the surface 10 against the surface 15 by means of planar device 7. Surface 15 also serves as a reference plane for the height 11 of the fine focus anode 16 of X-ray tube 1 and of slit apertured member 3 and cylinder apertured member 4. In this way, it is assured, structurally, that the tolerances, which are naturally small, with angles of only a few arc minutes, can be maintained. During the measuring process, wafer surface 10 only comes in contact with the quartz of the block-shaped quartz body 6, a material which assures maximum prevention against contamination.

Channels 116, 17, for example, are provided for the radiation 9, and a bore 18 is provided to receive the apertured member 4 detector mount 12, are provided in face 15.

It is the purpose of slit aperture member 3 to assure that the X-ray radiation 9 be unable to penetrate into the side edge of wafer 2 and that it impinge instead only on the surface 10 of the wafer. As seen in FIG. 1, a blocking portion 33 of the slip aperture member 3 blocks radiation from entering the left-hand side face of the wafer 2. Under the given conditions, the X-ray radiation 9 is reflected almost completely from the surface 10. However, positioning pressing piston device 8 is additionally controlled so that the gap between slit aperture member 3 and the edge of the wafer, which is unavoidable due to the circular shape of the wafer, is minimized at every measuring location on wafer 2. As seen in the alternative embodiment shown in FIG. 3, an apertured member 4, includes an aperture therein below detector 5 and is secured to a metal cylinder 12' whose bottom 50' forms an annular aperture 19 of a heavy metal, e.g. tantalum, for detector 5 (FIG. 3) positioned over the aperture 19 in apertured member 4. A gap 43' is shown between portions 42' and 43' of the apertured member 4', to permit fine adjustment. The height of this aperture 19 above wafer surface 10 is set to a few $\mu$m by means of screws 20 which operate against a bias and vertically move apertured member 4' and the cylinder 12 attached thereto. Connections 46 connect the tube 12' to the portion 41'.

The apertured member 4' and aperture 19 define exactly the section of wafer surface 10 to be tested. The primary accomplishment, however, is that, first, the stray radiation in the air and, second, the annoying flourescence radiation of the noble gases argon and krypton, as components of the air, be reduced to a minimum. With the novel apertured member 4 and aperture 19, whose use becomes possible only because of the extremely flat angle of incidence of the X-ray radiation, favorable conditions are realized at comparatively less expense than with evacuation of the sample chamber.

In addition to the possibility of on-line measuring of metal surface impurities of wafers 2, a further advantage provided by the invention makes it possible to vary the angle of incidence of the primary X-ray radiation 9 by merely changing the height 11 of the X-ray tube 1. In this manner, the measuring process is able to differentiate between the uppermost surface layer (about 10 nm with angles of incidence noticeably below the limit angle of total reflection) and the structure closely below the surface 10 (about 100 to 1000 nm for angles around the limit angle of total reflection).

Evidence is furnished in FIGS. 4 and 5 by the measured results from a surface 10 which was implanted (implantation depth about 50 nm) with $10^{12}$ nickel atoms per cm$^2$. The K radiation of an Mo tube was used for excitation. FIG. 4 herein shows the metal impurities of the immediate surface 10, measured with an angle of incidence of 1 to 3 arc minutes. The same location, measured with an angle of incidence of about 6 arc minutes (FIG. 5) additionally exhibits a clear Ni signal originating from a layer lying approximately 50 nm below surface 10.

The measured results are explained by theoretical calculations according to the dispersion theory for the total reflection of X-rays. FIGS. 6a to 6c and 7a to 7c show the results of calculations for two configurations corresponding to structures according to the present invention. FIG. 6a shows the intensity distribution of the radiation 9 impinging on wafer 2 at angles of incidence for a setting clearly below the limit angle of total reflection. FIG. 6b shows the distribution of the penetration depth for radiation 9 falling into the region of about 10 mm cut out by the aperture member (shaded in FIG. 6a). FIG. 6c shows the intensity of the exciting radiation 9 in wafer surface 10.

FIGS. 7a to 7c show the corresponding results for a setting in the vicinity of the limit angle for total reflection.

The invention now being fully described, it will be apparent to one of ordinary skill in the art that many changes and modifications can be made thereto without departing from the spirit of scope of the invention as set forth herein.

The present disclosure relates to the subject matter disclosed in German Application No. P 36 06 748.2 of Mar. 1, 1986 date, the entire specification of which is incorporated herein by reference.

We claim:

1. Arrangement for the non-destructive measurement of metal traces in the surface of material samples in which the surface is charged with X-ray radiation so that the radiation emanating from the material sample can be detected and spectrometrically examined, with said X-ray radiation sweeping over the surface of the material sample from an adjustable X-ray source oriented onto the surface of the material sample, comprising:

(a) a support member comprising a quartz body having a generally flat surface contacting a face of a material sample;

(b) a first support means for adjustably positioning a radiation detector relative to support member;

(c) a limiting means for limiting the exciting X-ray radiation to impinge on a surface region of the material sample (d) a radiation detector which is supported by said first support means; said limiting means being disposed on said generally flat surface of said support member which serves as an optical bench (e) a positioning means for pressing said material sample against said generally flat surface of said quartz body, said positioning means comprising a first pressing means for pressing against a portion of said material sample and a second pressing means for pressing another portion of said material sample against said flat surface.

2. Arrangement as defined in claim 1, wherein said limiting means includes a split aperture member, and wherein said quartz body has a generally cylindrical aperture, and further comprising:

an adjusting means for adjustably supporting said radiation detector within said generally cylindrical aperture relative to a surface of said material sample which is to be examined; and a means for adjusting said slit aperture member with respect to the surface of said material sample.

3. Arrangement as defined in claim 1, wherein said support member includes a generally cylindrical aperture accommodating said radiation detector.

4. Arrangement as defined in claim 2, wherein said support member includes a generally cylindrical aperture accommodating said detector.

5. Arrangement as defined in claim 2, wherein said generally flat surface has a slit therein which extends linearly along said generally flat surface and said slit aperture member blocks radiation from entering said material sample when said material sample is in contact with said generally flat surface, such that the radiation travels along said slit at a relatively small angle of incidence to said material sample.

* * * * *